United States Patent [19]

Turner

[11] Patent Number: 5,688,752
[45] Date of Patent: Nov. 18, 1997

[54] AQUEOUS PERSONAL CARE CLEANSER COMPRISING SPECIFIC LIPID COMPOSITION

[75] Inventor: Graham Andrew Turner, Wirral, United Kingdom

[73] Assignee: Lever Brothers Company, Division of Conopco, Inc., New York, N.Y.

[21] Appl. No.: 545,490

[22] Filed: Oct. 19, 1995

[30] Foreign Application Priority Data

Oct. 20, 1994 [GB] United Kingdom ............... 9421185

[51] Int. Cl.$^6$ ............... C11D 3/60; C11D 17/00; A61K 7/48; A61K 7/50
[52] U.S. Cl. ............... 510/159; 424/401; 424/450; 510/108; 510/130; 510/137; 510/138; 510/158; 510/417; 510/436; 510/437; 510/461; 510/467; 510/470; 510/473; 510/475; 510/501; 514/846
[58] Field of Search ............... 510/130, 136, 510/137, 138, 159, 158, 417, 437, 436, 470, 488, 505, 423, 433, 473, 475, 476, 468, 434, 108, 461, 501; 514/846; 424/401, 450

[56] References Cited

U.S. PATENT DOCUMENTS

| | | | |
|---|---|---|---|
| 4,673,525 | 6/1987 | Small et al. | 510/151 |
| 4,708,813 | 11/1987 | Snyder | 424/43 |
| 4,806,262 | 2/1989 | Snyder | 510/140 |
| 4,812,253 | 3/1989 | Small et al. | 510/151 |
| 4,976,953 | 12/1990 | Orr et al. | 424/47 |
| 5,002,680 | 3/1991 | Schmidt et al. | 510/140 |
| 5,096,608 | 3/1992 | Small et al. | 510/153 |
| 5,260,051 | 11/1993 | Cho | 424/57 |
| 5,308,526 | 5/1994 | Dias et al. | 510/159 |

FOREIGN PATENT DOCUMENTS

| | | |
|---|---|---|
| 0474023 | 3/1992 | European Pat. Off. . |
| 0487958 | 6/1992 | European Pat. Off. . |
| 0556957 | 8/1993 | European Pat. Off. . |
| 0587288 | 3/1994 | European Pat. Off. . |
| 63-192703 | 8/1988 | Japan . |
| 2250998 | 6/1992 | United Kingdom . |
| 90/01323 | 2/1990 | WIPO . |
| 94/00127 | 1/1994 | WIPO . |

OTHER PUBLICATIONS

International Search Report for PCT/EP95/03967, dated Feb. 15, 1996.

*Primary Examiner*—Ardith Hertzog
*Attorney, Agent, or Firm*—Ronald A. Koatz

[57] ABSTRACT

A personal care composition in the form of an aqueous liquid comprises:

i) a lipid composition comprising three components A, B and C,
where A is a molecule having at least two hydrocarbon chains and a polar head group for which $$0.5 < \frac{V}{a_o l_c} \leq 1.0;$$

B is a molecule having one long chain and a polar head group; and
C comprises a compound capable of assisting the formation of lipid bilayers and stabilizing any lipid bilayers formed in the lipid composition; and the molar ratio of A:B:C is 1.0:1.5 to 6.0:1.1 to 8.0;

ii) a surface active agent selected from anionic, nonionic, cationic, zwitterionic, amphoteric surface active agents, soap and mixtures thereof; and iii) a deposition aid.

The composition may in the form of for example a shower gel or facial cleanser which is temporarily applied to the skin before being removed such as wiping or rinsing it from the skin.

10 Claims, No Drawings

AQUEOUS PERSONAL CARE CLEANSER COMPRISING SPECIFIC LIPID COMPOSITION

The invention relates to a personal care composition in liquid or gel form suitable for personal washing. In particular, it is concerned with compositions, intended for washing and/or cleansing of the human skin, which prevent or ameliorate skin dryness, skin wrinkling, chapping and ageing.

It is generally understood that ceramides present within the intercellular lipid lamellae of the stratum corneum play an important role in the production and maintenance of the water permeability barrier of the skin. Ceramides, or substances closely related to them, have been disclosed as components of skin care compositions. In particular, Kao Corporation in GB 2178312 and GB 2213723 discloses the use of natural ceramides extracted from skin in products for topical application. Also, Kao Corporation in EP 227994 and EP 282816 discloses the use of synthetic ceramides, which are similar to their natural counterparts found in skin.

It is also known that, in addition to ceramides, the lipid lamellae comprises sterol and fatty acids (N Y Schurer, P M Elias (1991) Adv Lip Res 24 27–56 Acad Press).

It is believed that one of the causes of skin drying and ageing is a reduction in the amount of lipid contained within intercellular lipid lamella of the stratum corneum. It has been shown in intermolecular and Surface Forces, (1985) Jacob N Isrealachvili, ed Acad Press, Chapter 16 entitled "Aggregation of Amphiphilic Molecules into Micelles, Bilayers, Vesicles and Biological Membranes" that suitable lipids for forming a bilayer are those having a polar head group and at least two hydrocarbon chains, such that there exists a clearly defined relationship between the volume occupied by the hydrocarbon chains and the optimum area occupied by the polar head group. This relationship is that:

$$\frac{V}{a_o l_c}$$

should be greater than 0.5 but less than or equal to 1.0 where
V is the volume of the hydrocarbon chains
$l_c$ is the critical length of the hydrocarbon chains
$a_o$ is the optimum area of the polar head group.

EP-A-556 957 discloses compositions which satisfy the aforementioned relationship comprising (a) ceramides, (b) long chain fatty acids and a third component (c), for example squalene, which is capable of assisting and stabilising lipid bilayers formed in the composition and where the ratio of a:b:c is from 1:1.5 to 6.0:1.1 to 8.0 respectively. The disclosed compositions are intended for topical application to the human, hair, skin or nails. In particular they are "leave-on" products which are intended to be permanently applied to the hair, skin or nails.

WO 94/00127 also discloses three component lipid compositions which may be combined with an aqueous phase containing a surface active agent. Like EP-A-557 957, the compositions disclosed in this reference are intended as "leave-on" products.

There is a continued need for products which are able to successfully replace depleted lipids. Surprisingly it has now been found that lipid compositions comprising ceramides and related components; molecules having one long hydrocarbon chain and a polar head group, for example long chain fatty acids; and a third component which is capable of assisting and stabilising lipid bilayers formed in the composition can be formulated with surfactants to form a personal care composition which is intended to be temporarily applied to the skin before being rinsed or wiped off and that these personal care compositions provide an effective control of water loss and/or repair of damage to the water barrier layer in the stratum corneum.

The prior art compositions are intended as "leave-on" products which are not wiped or rinsed off. A disadvantage with such compositions is that they may leave the skin feeling oily.

The compositions of the present invention overcome this problem and offer a further advantage in that they are dual purpose compositions which, in use, provide both a skin washing/cleansing and a skin treatment benefit and which are only temporarily applied to the skin before being removed.

Thus, according to the invention there is provided a personal care composition in the form of an aqueous liquid comprising i) a lipid composition comprising three components A, B and C,
  where A is a molecule having at least two hydrocarbon chains and a polar head group for which $$0.5 < \frac{V}{a_o l_c} \leq 1.0;$$

B is a molecule having one long hydrocarbon chain and a polar head group; and
  C comprises a compound capable of assisting the formation of lipid bilayers and stabilising any lipid bilayers formed in the lipid composition; and the molar ratio of A:B:C is 1.0:1.5 to 6.0:1.1 to 8.0 respectively;

ii) a surface active agent selected from anionic, nonionic, cationic, zwitterionic, amphoteric surface active agents, soap and mixtures thereof; and iii) a deposition aid.

Component A

Component A is a molecule having at least two hydrocarbon chains and a polar head group, providing that the volume occupied by the hydrocarbon chains and the area occupied by the polar head group fulfils the relationship $$0.5 < \frac{V}{a_o l_c} \leq 1.0;$$

where V, $l_c$, and $a_o$ are defined above.

Preferably the hydrocarbon chains each have at least 14 carbon atoms. Furthermore, it is preferred that hydrocarbon chains having less than 16 carbon atoms are fully saturated, however, hydrocarbon chains having more than 16 carbon atoms may contain 1 to 3 unsaturations if desired.

Suitable polar head groups may be selected from residues such as phosphates, phosphonates, sulphates, sulphonates, sulphones, hydroxyl, ethylene oxide, carboxyl and mixtures thereof. Preferably the polar head group is selected from hydroxyl groups, ethylene oxide units, carboxyl groups and mixtures thereof.

Suitable compounds that may be selected as component A are ceramides; pseudoceramides; phospholipids; glycolipids having a structure of two or more acyl or alkyl long chains suitably containing from 14 to 50 carbon atoms each, attached to a polar group; specific esters of polyethylene glycol; polyglycerol-n-x oleate (CAS 9007-48-1); sorbitan dioleate (CAS 29116-98-1); sorbitan sesquioleate (CAS 8007-43-0); long chain alkyl ether versions of phospholipids and glycolipids; and mixtures thereof.

Ceramides

Ceramides are preferably selected from ceramides having the general structure (1)

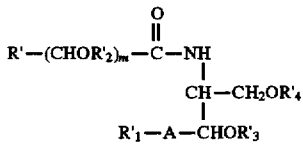

where A represents —CH$_2$—; CHOR'$_5$—; —CH=CH— or —CHOY—

R' represents a linear or branched, saturated or unsaturated aliphatic hydrocarbon group having from 1 to 49 carbon atoms, preferably from 12 to 49 carbon atoms, or a subgroup (2).

R'$_1$ represents a linear or branched, saturated or unsaturated aliphatic hydrocarbon group having from 8 to 28 carbon atoms, preferably from 13 to 28 carbon atoms;

R'$_2$, R'$_3$, and R'$_5$ individually represent H, a phosphate residue or a sulphate residue;

R'$_4$ represents H, a phosphate residue, a sulphate residue or a sugar residue;

a is an integer of from 7 to 49, preferably from 12 to 49;

b is an integer of from 10 to 98, preferably from 24 to 98;

m is 0 or 1;

Y represents H or a residue of a C$_{14-22}$ fatty acid having the general structure (3).

where

Z is —OH or an epoxy oxygen x is an integer of from 12 to 20 y is an integer of from 20 to 40 and z is 0 or an integer of from 1 to 4

Ceramides having the general structure (1) are naturally occurring and can be isolated from a suitable plant source or from animal tissue such as pig skin or neural tissue. Ceramides can also be synthesised.

Particular preferred examples are ceramides I, II and II.

Pseudoceramides

Pseudoceramides are preferably selected from pseudoceramides (ie synthetic ceramide like structures) having the general structure (4);

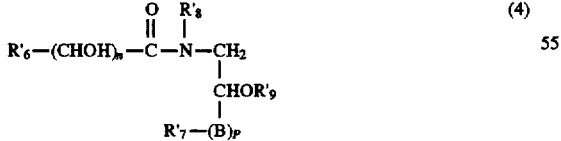

where B represents —OCH$_2$— or CHOH;

R'$_6$ represents a linear or branched, saturated or unsaturated aliphatic hydrocarbon group having from 1 to 49 carbon atoms, preferably from 12 to 49 carbon atoms or the subgroup (2).

R'$_7$ represents a linear or branched, saturated or unsaturated aliphatic hydrocarbon group having from 8 to 28 carbon atoms preferably from 13 to 28 carbon atoms.

R'$_8$ represents H, or a subgroup —(CH$_2$)$_c$COOH, where c is an integer of from 1 to 6, or a subgroup having the structure (5).

where X$_1$, X$_2$ and X$_3$ each individually represent H, a C$_{1-5}$ alkyl or a C$_{1-5}$ hydroxyalkyl;

d is 0 or an integer of from 1 to 4 e is 0or 1 n is 0 or 1 and p is 0 or 1;

R'$_9$ represents H, a phosphate residue, a sulphate residue or a sugar residue.

Phospholipids

Phospholipids may be advantageously used because they are derivable from plant sources. An example of a suitable phospholipid material is a mixture of phospholipids derived from a particular fraction in a continuous soya bean phospholipid extraction and is sold under the trade name Ceramax by Quest International of Ashford, Kent, UK.

Glycolipids

Suitable glycolipids are those having a structure of two or more acyl or alkyl long chains suitably containing from 14 to 50 carbon atoms each, attached to a polar head group. The polar head group may be selected from residues such as phosphates, phosphonates, sulphates, sulphonates, sulphones, hydroxyl, ethylene oxide, carboxyl and mixtures thereof. Preferably the polar head group is hydroxylated.

Suitable examples are glycosyl glycerides or diacyl or dialkyl saccharides, eg sucrose diesters with two or more long chain ester groups. An example of the latter type of material is obtainable from Ryoto under the appellation Ryoto sugar esters such as Ryoto sugar ester S270, and S1570.

Esters of Polyethylene Glycol

Suitable esters are:

(i) succinic acid esters having the general structure (6)

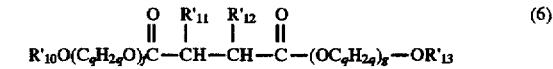

in which R'$_{10}$ represents an alkyl, alkenyl, mono- or dihydroxyalkyl or hydroxyalkenyl group having from 6–22 carbon atoms;

R'$_{11}$ and R'$_{12}$ individually represent H or an alkyl or alkenyl group having from 12 to 22 carbon atoms;

providing that when R'$_{11}$ is H; R'$_{12}$ is an alkyl or alkenyl group and when R'$_{12}$ is H; R'$_{11}$ is an alkyl or alkenyl group;

R'$_{13}$ represents hydrogen, an alkyl, alkenyl, mono- or dihydroxyalkyl or hydroxyalkenyl group having from 6 to 22 carbon atoms or the group (7):

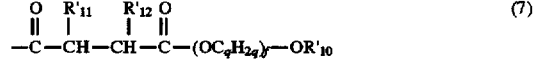

q is an integer of from 2 to 3 f and g are average degrees of alkoxylation, namely f is from 0 to 20 and g is from 1 to 20.

In structure (6), the group R'$_{13}$ preferably represents H, while the group R'$_{10}$ preferably represents an alkyl group having from 16 to 22 carbon atoms and most preferably from 20 to 22 carbon atoms.

Also with reference to structure (6), q is preferably 2 and (f+g) is preferably from 1 to 20.

Such succinic acid esters are synthesised using known methods of preparative chemistry, these methods are described in our patent application WO/94/10971.

(ii) Polyethylene glycol r-dilaurate (CAS 9005-02-1) and polyethylene glycol r-distearate (CAS 9005-08-7).

(iii) Polyethylene glycol r-distearammonium chlorides. These may be derived from polyethylene glycol r-tallow amine (CAS 61791) by alkylating the nitrogen with an alkyl halide having more than 8 carbon atoms.

(iv) Polyethylene glycol derivatives of long chain alkyl derivatives of malic, tartaric, maleic, malonic and glyceric acid.

where r is the number of ethylene oxide groups within the molecule and is preferably from 1 to 8, most preferably from 2 to 4.

Component B

Component B is a molecule having one long hydrocarbon chain and a polar head group. A wide variety of simple co-surfactants are functional as this component. Preferred co-surfactants are straight-chained mono carboxylic acids having 14 to 30 carbon atoms, straight-chained fatty alcohols having 14 to 30 carbon atoms, sugar esters, alkylated sugars and mixtures thereof. Examples of suitable sugar esters and alkylated sugars are monopalmitoyl or 6-cetyl glucose and α or β methyl 6-cetyl glucoside.

Preferably the co-surfactants are chosen from straight chained mono-carboxylic acids having 14 to 24 carbon atoms.

The mono-carboxylic acids may be used as 50–100% sodium or potassium soap.

A particularly preferred component B is linoleic acid, since linoleic acid assists in the absorption of ultraviolet light and furthermore is a vital component of the natural skin lipids constituting the moisture barrier in the stratum corneum.

Component B may comprise a mixture of compounds, for example a fatty acid mixture of palmitic, oleic and stearic acid at 3:2:1 by weight may be employed. However particularly useful fatty acids from the point of view of availability are linoleic and stearic acid.

Component C

Component C comprises a compound capable of stabilising any lipid bilayers which may be formed in the composition.

Suitable compounds may be selected from 3β-sterol; squalene; squalane; saponins or sapogenins of the plant steroid or triterpenoid type; di and tri terpenes such as phytol, retinol and amyrin; and mixtures thereof.

Preferably component C comprises a 3β-sterol having a tail on the 17 position and having no polar groups, for example cholesterol, sitosterol, stigmasterol and ergosterol. Commercially available sources of cholesterol include Super Hartolan ex Croda which comprises at least 30% cholesterol.

A particularly preferred component C is the 3β-sterol ergosterol since this is well known to convert in situ into vitamin $D_2$ (caciferol) on reception of ultraviolet light.

It is essential that the molar ratio in which the components A, B and C are present is from 1.0:1.5 to 6.0:1.1 to 8.0 respectively, in order to ensure adequate control of water flux.

Preferably the molar ratio in which the components A, B and C are present is from 1.0:1.5 to 4.0:1.0 to 4.0 respectively and, most preferably, from 1.0:1.8 to 3.6:1.2 to 3.0 respectively. Particularly preferred compositions are those in which the molar ratio of components A:B:C is 1:1:2.

The level of lipid composition in the personal care composition is preferably in the range 0.05 to 10% by weight, most preferably 0.1 to 5% by weight, based on the personal care composition.

The surface active agent can be selected from any known surfactant suitable for topical application to the human body. Mild surfactants, i.e. surfactants which do not damage the stratum corneum, the outer layer of skin, are particularly preferred.

One preferred anionic detergent is fatty acyl isethionate of formula:

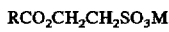

$$RCO_2CH_2CH_2SO_3M$$

where R is an alkyl or alkenyl group of 7 to 21 carbon atoms and M is a solubilising cation such as sodium, potassium, ammonium or substituted ammonium. Preferably at least three quarters of the RCO groups have 12 to 18 carbon atoms and may be derived from coconut, palm or a coconut/palm blend.

Another preferred anionic detergent is alkyl ether sulphate of formula:

$$RO(CH_2CH_2O)_nSO_3M$$

where R is an alkyl group of 8 to 22 carbon atoms, n ranges from 0.5 to 10 especially 1.5 to 8, and M is a solubilising cation as before or $Mg^{2+}$.

Other possible anionic detergents include alkyl glyceryl ether sulphate, sulphosuccinates, taurates, sarcosinates, sulphoacetates, alkyl phosphate, alkyl phosphate esters and acyl lactylate, alkyl glutamates, and mixtures thereof.

If the surface active agent comprises soap, the soap is preferably derived from materials with a $C_8$ to $C_{22}$ substantially saturated carbon chain and, preferably, is a potassium soap with a $C_{12}$ to $C_{18}$ carbon chain.

Sulphosuccinates may be monoalkyl sulphosuccinates having the formula: $R^5O_2CCH_2CH(SO_3M)CO_2M$; and amido-MEA sulphosuccinates of the formula: $R^5CONHCH_2CH_2O_2CCH_2CH(SO_3M)$; wherein $R^5$ ranges from $C_8$–$C_{20}$ alkyl, preferably $C_{12}$–$C_{15}$ alkyl and M is a solubilising cation.

Sarcosinates are generally indicated by the formula: $R^5CON(CH_3)CH_2CO_2M$, wherein R ranges from $C_8$–$C_{20}$ alkyl, preferably $C_{12}$–$C_{15}$ alkyl and M is a solubilising cation.

Taurates are generally identified by the formula: $R^5CONR^6CH_2CH_2SO_3M$, wherein $R^5$ ranges from $C_8$–$C_{20}$ alkyl, preferably $C_{12}$–$C_{15}$ alkyl, $R^6$ ranges from $C_1$–$C_4$ alkyl, and M is a solubilising cation.

Harsh surfactants such as primary alkane sulphonate or alkyl benzene sulphonate will generally be avoided.

Suitable nonionic surface active agents include alkyl polysaccharides, lactobionamides, ethyleneglycol esters, glycerol monoethers, polyhydroxyamides (glucamide), primary and secondary alcohol ethoxylates, especially the $C_{8-20}$ aliphatic alcohols ethoxylated with an average of from 1 to 20 moles of ethylene oxide per mole of alcohol.

Mixtures of any of the foregoing surface active agents may also be used.

The surface active agent is preferably present at a total level of from 1 to 45 wt %, preferably 3 to 30 wt %, and most preferably 5 to 20wt %.

It is also preferable that the composition includes from 0.5 to 15 wt % of a cosurfactant agent with skin-mildness benefits. Suitable materials are zwitterionic detergents which have an alkyl or alkenyl group of 7 to 18 carbon atoms and comply with an overall structural formula

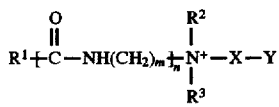

where $R^1$ is alkyl or alkenyl of 7 to 18 carbon atoms $R^2$ and $R^B$ are each independently alkyl, hydroxyalkyl or carboxyalkyl of 1 to 3 carbon atoms m is 2 to 4 n is 0 or 1

X is alkylene of 1 to 3 carbon atoms optionally substituted with hydroxyl, and

Y is $—CO_2^-$ or $—SO_3^-$

Zwitterionic detergents within the above general formula include simple betaines of formula:

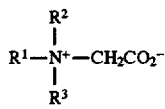

and amido betaines of formula:

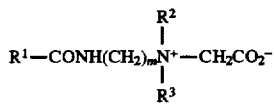

where m is 2 or 3.

In both formulae $R^1$, $R^2$ and $R^3$ are as defined previously.

$R^1$ may, in particular, be a mixture of $C_{12}$ and $C_{14}$ alkyl groups derived from coconut so that at least half, preferably at least three quarters of the groups $R^1$ have 10 to 14 carbon atoms. $R^2$ and $R^3$ are preferably methyl.

A further possibility is a sulphobetaine of formula:

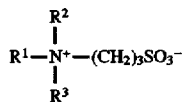

or

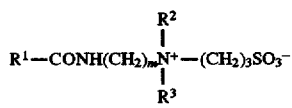

where m is 2 or 3, or variants of these in which $—(CH_2)_3SO_3^-$ is replaced by

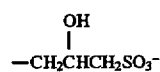

$R^1$, $R^2$ and $R^3$ in these formulae are as defined previously.

Preferably the deposition aid is a cationic polymer present in an amount of at least 0.05% by weight of the total composition. It may well not exceed 3% or even 2% of the composition.

Various cationic polymers may be used. Examples of cationic polymers include the cationic cellulose ethers described in U.S. Pat. Nos. 3,816,616 and 4,272,515 and which are available commercially from Union Carbide Corp. under the trade mark POLYMER JR. Other suitable materials are the cationic polygalactomannan gum derivatives described in U.S. Pat. No. 4,298,494 which are commercially available under the trade mark JAGUAR. An example of a suitable material is the hydroxypropyltrimethylammonium derivative of guar gum of the formula:

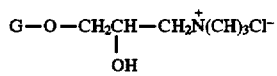

where G represents guar gum. Such a material is available under the name JAGUAR C-13-S. This material also has the CTFA designation Guar Hydroxypropyltrimonium Chloride. In JAGUAR C-13-S the degree of substitution of the cationic groups is about 0.13. Another possible material is that known as JAGUAR C-17 which is similar to JAGUAR C-13-S but has a higher degree of substitution of cationic groups of about 0.25–0.31. A further example of a guar derivative is the hydroxypropylated cationic guar derivative known as JAGUAR C-16 which as well as containing the above cationic quaternary ammonium groups also contain hydroxypropyl ($—CH_2CH(OH)CH_3$) substituent groups. In JAGUAR C-16 the degree of substitution of the cationic groups is 0.11–0.16 and the moles of substitution of hydroxypropyl groups is 0.8–1.1.

Other cationic polymers include cationic polyamides such as the low molecular weight adipic acid/diethylene-triamine polyamide and the copolymers of vinylpyrrolidone and dimethylaminoethyl methacrylate quaternised with dimethyl sulphate (Gafquat 755, GAF Corporation) described in U.S. Pat. No. 4,080,310; the graft cationic copolymer containing N-vinylpyrrolidone, dimethylaminoethyl methacrylate and polyethylene glycol described in U.S. Pat. No. 4,048,301; the mineral acid salts of the amino-alkyl esters of homo- and copolymers of unsaturated carboxylic acids having from 3 to 5 carbon atoms described in U.S. Pat. No. 4,009,256; the polymers of etherified starch described in U.S. Pat. No. 3,186,911; and cationic polyacrylamides of the type described in British Patent Application 9403156.4.

The high molecular weight cationic polymers are sold under the trade mark MERQUAT by Merck & Co., Inc. Representative are Merquat 100, a highly charged cationic dimethyldiallylammonium chloride homopolymer, and Merquat (™) 550, a highly charged cationic copolymer prepared with dimethyldiallylammonium chloride and acrylamide. These materials are designated in the CTFA dictionary as Quaternium-40 and Quaternium-41, respectively.

Preferred cationic polymers include cationic cellulose ethers, cationic polygalactomannan gums and cationic polyacrylamides.

Other typical optional components which may be included in the compositions of the invention are humectants such as glycerol up to 10wt %; opacifiers, preferably at a level of 0.2 to 2.0 wt %; preservatives, preferably 0.2 to 2.0wt % and perfumes, preferably 0.5 to 3.0wt %; bactercides; colourants; antioxidants; skin-feel modifiers; and thickeners and structurants such as swelling clays, crosslinked polyacrylates, for example, Carbopol (™) (polymers available from Goodrich) and polyethoxypropylene glycoldioleate.

Compositions of the invention may be formulated as products for washing the skin, for example bath or shower gels; hand-washing compositions; facial washing liquids; and skin cleansers.

Without being bound by theory it is believed that the deposition aid assists deposition of the lipid composition onto the skin.

The composition of the invention is intended, during use, to reduce the permeability of the skin to water, particularly when the skin is dry or damaged, in order to reduce moisture loss and generally enhance the quality and flexibility of the skin.

In use, the composition is temporarily applied to the skin directly or by the use of an applicator. It is then removed from the skin such as by rinsing with water, particularly in the case of showergels, or by wiping off such as with a tissue.

The composition according to the invention is preferably formulated as a liquid or gel having a viscosity in the range 1000 to 100 000 mPas measured at a shear rate of 10 s$^{-1}$ and 25° C. in a Haake Rotoviscometer RV20.

Compositions according to the invention may be prepared by melting the components of the lipid composition. Water is then added to the resultant lipid melt. The surface active agent is melted and then added to the lipid/water mixture. The resultant mixture is cooled before cationic polymer and optional components are added.

The composition may be packaged in a suitable container from which it can be dispensed directly onto the skin or via an applicator. The invention accordingly provides a closed container containing the personal care composition as herein defined.

The invention also provides for the use in a personal care composition which is temporarily applied to the skin of i) a lipid composition comprising three components A, B and C, where A is a molecule having at least two hydrocarbon chains and a polar head group for which $$0.5 < \frac{V}{a_o l_c} \leq 1.0;$$

B is a molecule having one long chain and a polar head group; and

C comprises a compound capable of assisting the formation of lipid bilayers and stabilising any lipid bilayers formed in the lipid composition; and the molar ratio of A:B:C is 1.0:1.5 to 6.0:1.1 to 8.0 respectively;

ii) a surface active agent selected from anionic, nonionic, cationic, zwitterionic, amphoteric surface active agents, soap and mixtures thereof; and iii) a deposition aid.

The invention will now be further illustrated by reference to the non-limiting examples.

EXAMPLES

In the examples:

Cationic polymer was guar hydroxypropyl trimonium chloride was Jaguar C-13-S ex Meyhall in examples 1 to 6 and 8. In example 7 it was a cationic polyacrylamide.

In examples 1 to 7 Cholesterol was cholesterol USP ex Croda.

In example 8 cholesterol was Super Hartolan ex Croda containing at least 30% cholesterol.

Coco amidopropyl betaine (CAPB) was Tegobetaine C ex Goldschmidt except in formulation VIII where it was Tegobetaine F ex Goldschmidt.

Decyl glycoside was Oramix NS10 ex Seppic.

Polyethoxypropylene glycodioleate was Antil 141 ex Goldschmidt.

Propylene glycol was ex BDH.

Sodium cocoisethionate was Jordapon SCI ex PPG/Mazer.

Sodium lauryl ether sulphate (SLES) was Elfan NS 243S ex Akzo.

Stearic acid was ex BDH.

Sucrose ester was Ryoto S-270 ex Mitsubishi-Kasei.

Compositions according to the examples were prepared by melting the components of the lipid composition by heating to approximately 70° C. The lipid components were heated in ethanol when it was present in the formulations. Water was then added at approximately 70° C. In a separate vessel the surface active agents were heated to approximately 70° C. before being added sequentially to the molten lipid mixture. The resultant surface active agent/lipid mixture was mixed and mixing continued whilst it was cooled to room temperature. The cationic polymer, predispersed in perfume, was then added followed by minor components. Finally the pH of the composition was adjusted. When the formulations contained glycerol this is used at the initial lipid melt stage replacing the ethanol.

Example 1

Compositions formulated according to the invention and comparative compositions were tested by visual assessment of skin dryness and erythema of treated skin and measuring the reduction in water flux.

The experimental procedure employed was as follows. This was carried out on 24 human volunteers.

Both forearms of a human volunteer were washed with a control shower gel of formulation C, given below, three times a day for 7 days. The forearms were wetted with warm water and the shower gel was dispensed directly onto the arm and then rubbed into a lather for 45 seconds. The forearms were then rinsed with warm water for 15 seconds before being patted dry. They were monitored for skin dryness and erythema on a daily basis.

On days 8–12 the volunteers forearms were washed with a composition formulated according to the invention (I or II) or a control four times a day. (Formulations are given below in Table 1). The forearms were wetted with warm water and the shower gel was dispensed directly onto the arm and then rubbed into a lather for 45 seconds. The forearms were then rinsed with warm water for 15 seconds before being patted dry. They were monitored for skin dryness and erythema on a daily basis. On day 13 only three washes were performed.

This test procedure can be used to assess the effectiveness of the compositions according to the invention in alleviating dryness produced during the first 7 days of the test.

| Formulation C | % by wt |
| --- | --- |
| SLES | 13.0 |
| CAPB | 2.0 |
| NaCl | 1.5 |
| Perfume, preservative, minors and water | to 100 |

TABLE I

| Formulation | % by weight | | |
| --- | --- | --- | --- |
| | I | II | Control |
| SLES | 12.00 | 12.00 | 12.00 |
| CAPB | 3.00 | 3.00 | 3.00 |
| Cholesterol | 2.50 | 0.50 | — |
| Sucrose ester | 1.25 | 0.25 | — |
| Stearic acid | 1.25 | 0.25 | — |

TABLE I-continued

| | % by weight | | |
|---|---|---|---|
| Formulation | I | II | Control |
| Propylene glycol | 5.00 | 0.25 | — |
| Cationic polymer | 0.25 | 0.25 | — |
| Polyethoxypropylene glycodioleate | 3.00 | 3.00 | 3.00 |
| NaOH to adjust pH to 6.0 ± 0.5 | | | |
| Water + preservative ← to 100 → | | | | i) Skin dryness and erythema

This was assessed visually and scored as below.

| Skin Dryness | Score |
|---|---|
| No visible dryness | 0 |
| Slightly white, barely perceptible | 1 |
| Moderate whiteness: | 2 |
| Slight patchy uplifting of skin | 3 |
| Sight uplifting of skin, uniform scaling | 4 |

| Erythema | Score |
|---|---|
| None | 0 |
| Barely perceptible | 0.25 |
| Slight | 0.50 |
| Mild/patchy | 1.0 | ii) Reduction in water flux (Trans Epidermal Water loss —TEWL).

TEWL measurements were carried out using a Servomed Evaporimeter EP1 on a fixed site on each of the volunteer's arms (arbitrarily set at 5 inches from the wrist). Measurements were taken i) prior to the start of trial;

ii) immediately prior to first wash on day 8; and iii) at least 1 hour after the last wash on day 13.

A Teflon probe, containing two sensors, was rested on the surface of the skin. These sensors measured the partial water vapour pressure at two distances above the skin surface. The read out from the equipment gave the rate of water evaporation from the skin surface.

The following results were obtained:

TABLE II

| Formulation | I | II | Control |
|---|---|---|---|
| Erythema | | | |
| Day 8 | 0.03 | 0.00 | 0.04 |
| Day 13 | 0.30 | 0.28 | 0.57 |
| Dryness | | | |
| Day 8 | 1.68 | 1.84 | 1.62 |
| Day 13 | 1.59 | 2.03 | 2.16 |
| TEWL/g/m²/h | | | |
| Day 8 | 8.84 | 8.82 | 9.20 |
| Day 13 | 11.27 | 11.82 | 12.90 |

The visual dryness demonstrated that formulation I resulted in significantly lower dryness than the control ($P<0.05$).

The TEWL results demonstrated that formulations I and II, according to the invention, gave rise to a slower breakdown of the stratum corneum barrier function (as shown by an increase in water flux) than the control. This was found to be statistically significant ($P<0.05$).

Example 2

In this example the amount of lipid deposited onto skin after it had been washed with compositions according to the invention was determined.

The following method was used to determine the amount of lipid deposited onto the skin of a human volunteer.

The volunteers washed their forearms with a shower gel. The procedure involved wetting the arm and also the volunteer's free hand with warm water then using the free hand to lather the arm with 0.5 ml of formulation III for 10 seconds, next rinsing for 10 seconds while rubbing with the free hand and then drying the arm with a single pass with a paper towel.

10 minutes after drying the forearm a glass cylinder was applied to two areas of skin on the forearm. The skin enclosed by the cylinder (10 $cm^2$) was extracted three times with 1 ml of ethanol. The amount of cholesterol in the extract was determined using an enzymatic kit from Sigma (352-20). This procedure was repeated with each formulations IV–VI.

Prior to treatment with the test product skin was extracted to determine the amount of cholesterol in untreated skin. The amount of cholesterol in skin treated with the following control formulation was also determined.

TABLE III

| Formulation | III | IV | V | VI | Control |
|---|---|---|---|---|---|
| | WT % | | | | |
| SLES | 12.00 | 12.00 | 12.00 | 12.00 | 12.00 |
| CAPB | 3.00 | 3.00 | 3.00 | 3.00 | 3.00 |
| Polyethoxypropylene glycodioleate | 3.00 | 3.00 | 3.00 | 3.00 | 3.00 |
| Sucrose ester | 0.5 | 0.75 | 1.00 | 1.25 | — |
| Cholesterol | 1.00 | 1.50 | 2.00 | 2.50 | — |
| Stearic Acid | 0.50 | 0.75 | 1.00 | 1.25 | — |
| Cationic polymer | 0.25 | 0.25 | 0.25 | 0.25 | — |
| Ethanol | 1.00 | 1.00 | 1.00 | 1.00 | 1.00 |
| NaOH to adjust pH to 6.0 ± 0.5 | | | | | |
| Water + preservative ← to 100 → | | | | | |

The following results were obtained

| Formulation | Cholesterol (ug/10 $cm^2$) |
|---|---|
| None | 12.3 |
| Control | 8.7 |
| III | 12.2 |
| IV | 17.17 |
| V | 23.5 |
| VI | 18.7 |

The results demonstrate that treatment with the Control results in a decrease in the stratum corneum barrier lipid (i.e. cholesterol). When the ternary lipid composition was added to the control formulation at levels at 1% and above there was an increase in the amount of cholesterol detected above that found on untreated skin, demonstrating that the compositions of the invention were effective in depositing lipid onto the skin.

Example 3

In this example the effect of cationic polymer on deposition of lipid onto porcine full thickness skin of the compositions according to the invention was determined.

The compositions used in this example were the control and formulation VI given above. For comparison purposes experiments were also carried out with formulation VI but from which the cationic polymer was omitted.

0.3 ml of the compositions, diluted with tap water at a ratio of 1:4 with tap water (to simulate "in-use" conditions) were then applied to separate pieces of the skin (5×5 cm). The compositions were rubbed into the skin for 50 rubs, rinsed with water for 10 seconds and then patted dry with a paper towel. The skin was then extracted with ethanol as described above to determine the amount of cholesterol deposited onto it.

The following result were obtained:

| Formulation | Cholesterol ($\mu g/10\ cm^2$) |
|---|---|
| None | 19.8 |
| Control | 9.5 |
| Formulation VI | 29.6 |
| Formulation VI but with no cat. polymer | 17.2 |

The results demonstrate the benefit of including a cationic polymer in the compositions of the invention

Example 4

Example 2 was repeated with formulation VII (this was identical to formulation VI except sucrose ester was replaced by Ceramide II (formula 8)).

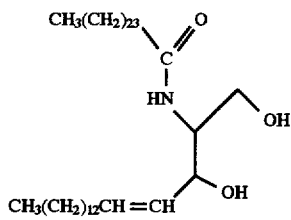
8

The following results were obtained:

| Formulation | Cholesterol ($\mu g/10\ cm^2$) |
|---|---|
| None | 9.6 |
| control | 7.6 |
| *formulation VII | 15.1 |

The results demonstrate that treating the skin with the control formulation has an adverse effect on the stratum corneum resulting in loss of some of the barrier lipid. The addition of a ternary lipid compositions to control C results in an increase in the level of lipid deposited and it is expected that this would lead to an improvement in the barrier properties of the skin (ie reduced skin dryness and lower TEWL.)

Example 5

Example 2 was repeated with the formulations given in Table IV, i.e. a different surfactant system was used.

TABLE IV

| Formulation | Control wt % | VIII |
|---|---|---|
| Sodium cocoisethionate | 5.0 | 5.0 |
| SLES | 2.0 | 2.0 |
| CAPB | 8.0 | 8.0 |
| Cationic polyiner | 0.25 | 0.25 |
| Cholesterol | — | 2.50 |
| Sucrose ester | — | 1.25 |
| Stearic Acid | — | 1.25 |
| Ethanol | 1.00 | 1.00 |
| Preservatives, minors + water ← to 100 → | | |

The following results were obtained:

| Formulation | Cholesterol ($\mu g/10\ cm^2$) |
|---|---|
| None | 11.4 |
| Control | 8.0 |
| VIII | 14.8 |

Example 6

Example 2 was repeated with the formulations given in Table V in which the only surface active agent was an alkyl polyglycoside.

TABLE V

| Formulation | Control wt % | IX |
|---|---|---|
| Decyl glucoside | 15 | 15 |
| Cationic polymer | 0.25 | 0.25 |
| Cholesterol | — | 2.50 |
| Sucrose ester | — | 1.25 |
| Stearic Acid | — | 1.25 |
| Ethanol | 1.00 | 1.00 |
| Preservatives, minors + water ← to 110 → | | |

The following results were obtained:

| Formulation | Cholesterol ($\mu g/10\ cm^2$) |
|---|---|
| None | 11.4 |
| Control | 10.0 |
| IX | 19.3 |

The results obtained in examples 5 and 6 were similar to those obtained in example 2, demonstrating the effect of the ternary lipid composition was independent of the surface active agents present in the base formulation.

Example 7

Example 3 was repeated except the cationic polymers in this example were various cationic polyacrylamides, characterised by their charge density and intrinsic viscosity. The formulation of the composition used in this example is given in Table VI.

TABLE VI

| Formulation | X wt % | Control |
|---|---|---|
| SLES | 12.00 | 12.00 |
| CAPB | 3.00 | 3.00 |
| Cholesterol | 2.50 | — |
| Sucrose ester | 1.25 | — |
| Stearic Acid | 1.25 | — |
| Propylene glycol | 5.00 | 5.00 |
| Cationic Polymer | 0.10 | 0.10 |
| Polyethoxypropylene glycoldioleate | 3.00 | 3.00 |
| NaOH to adjust pH to 6.0 ± 0.5 | | |
| water + preservative ← to 100 → | | |

| Cationic Polymer | | |
|---|---|---|
| Charge Density (meq/g) | Intrinsic Viscosity (dl/g) | Deposition Cholesterol (μg/10 cm$^2$) |
| 1.452 | 11.3 | 25.9 |
| 1.452 | 12.5 | 25.8 |
| 1.941 | 8.0 | 32.7 |
| Control (no cationic polymer) | | 19.9 |

Like example 3; these results demonstrated the benefit of incorporating a cationic polymer in the compositions.

Example 8

Compositions formulation according to the invention and comparative compositions were tested by visual assessment of skin dryness of treated skin and measuring the reduction in water flux using the methods described in example 1.

In this example Corneometer readings were also taken at the same time as the TEWL readings. The procedure involved resting a conductance probe on the skin surface for a few seconds. The value obtained provided a measure of the hydration state of the outer layer of skin.

Both forearms of a human volunteer were washed with a 80/20 Tallow/Coconut commercially available soap bar up to three times a day for 7 days. The foreams were wetted with warm water and the soap bar rubbed up and down the foreams for a total of 10 strokes. Lather was then generated for 45 seconds. The foreams were then rinsed with warm water for 15 seconds before being patted dry. They were monitored for skin dryness and erythema on a daily basis. The forearms were constantly monitored during this seven day period to ensure no erythema developed. If erythema developed the total number of washes was reduced to minimise erythema. Only those volunteers whose forearms scored at least 2.5 on the skin dryness scale, defined above, prior to the first wash on day 8 were used in the test.

On days 8 to 12 the volunteers forearms were washed with a composition formulated according to the invention or a control four times a day using the procedure described above for example 1. (Formulations are given below in Table VII).

TABLE VII

| Formulation | XI | C1 | XII | C2 | XIII | C3 |
|---|---|---|---|---|---|---|
| | % by weight | | | | | |
| SLES | 13.0 | 13.0 | 16.0 | 16.0 | 16.0 | 16.0 |
| CAPB | 2.0 | 2.0 | 2.0 | 2.0 | 2.0 | 2.0 |
| Cholesterol | 2.50 | — | 2.50 | — | 2.50 | — |
| Sucrose ester | 1.25 | — | 1.25 | — | 1.25 | — |
| Stearic Acid | 1.25 | — | 1.25 | — | 1.25 | — |
| Cationic polymer | 0.25 | 0.25 | 0.25 | 0.25 | 0.25 | 0.25 |
| Glycerol | — | — | — | — | 5.00 | 5.00 |
| Water + preservatives + minors ← 100 → | | | | | | |

The following results were obtained.

TABLE VIII

| FORMULATION | XI | CI | XII | C2 | XIII | C3 |
|---|---|---|---|---|---|---|
| DRYNESS | | | | | | |
| Day 8 | 2.91 | 3.09 | 2.65 | 2.56 | 3.00 | 3.05 |
| Day 13 | 2.57 | 3.08 | 2.21 | 2.70 | 2.10 | 2.49 |
| TEWL/g/m$^2$/h | | | | | | |
| Day 8 | 9.17 | 9.83 | 9.58 | 9.70 | 6.76 | 6.53 |
| Day 13 | 10.70 | 12.55 | 10.96 | 13.15 | 7.47 | 8.33 |
| P Value | | 0.0059 | | 0.0013 | | <0.001 |
| HYDRATION (CORNEOMETER) | | | | | | |
| Day 8 | 61.58 | 61.97 | 58.52 | 55.86 | 56.95 | 55.2 |
| Day 13 | 58.6 | 52.56 | 59.35 | 54.69 | 63.63 | 58.14 |
| P Value | | 0.0007 | | <0.001 | | 0.0003 |
| n | | 22 | | 22 | | 17 | n is the number of volunteers who took part in the test.

We claim:

1. A personal care cleansing composition in the form of an aqueous liquid comprising:

(i) a lipid composition comprising three components A, B and C, where A is a molecule having at least two hydrocarbon chains and a polar head group for which $$0.5 < \frac{V}{a_o l_c} \leq 1.0$$

wherein V is the volume of the hydrocarbon chains, $l_c$ is the critical length of the hydrocarbon chains, and $a_o$ is optimum area of the polar head group;

B is a molecule having one long chain and a polar head group; and

C comprises a compound selected from the group consisting of 3β-sterol, squalene, squalane, saponins or sapogenins derived from the plant steroid or triterpenoid, di- and triterpenes; and mixtures thereof; and the molar ratio of A:B:C is 1.0:1.5 to 6.0:1.1 to 8.0;

(ii) a surface active agent separate from any surfactant defined by component (i) selected from the group consisting of anionic, nonionic, cationic, zwitterionic, amphoteric surface active agents, soap and mixtures thereof; and (iii) a deposition aids;

wherein total synthetic surfactant (ii) is greater than amount of soap, if any present.

2. A personal care composition according to claim 1 wherein component A is selected from the group consisting of ceramides; pseudoceramides; phospholipids; glycolipids having a structure of two or more acyl or alkyl long chains containing from 14 to 50 carbon atoms attached to a polar head group; esters of polyethylene glycol; polyglycerol-n-x-oleate; sorbitan dioleate; sorbitan sesquioleate; long chain alkyl ethers of phospholipids and glycolipids; and mixtures thereof.

3. A personal care composition according to claim 2 wherein component A is selected from the group consisting of glycosyl glycerides, diacyl saccharides and dialkyl saccharides.

4. A personal care composition according to claim 1 wherein component B is selected from the group consisting of straight chained mono-carboxylic acids having 14 to 24 carbon atoms.

5. A personal care composition according to claim 1 wherein component C is a 3β sterol component which is cholesterol.

6. A personal care composition according to claim 1 wherein the deposition aid is a cationic polymer.

7. A personal care composition according to claim 6 wherein the cationic polymer is selected from the group consisting of cationic cellulose ethers, cationic polygalactomannan gums, cationic polyacrylamides and mixtures thereof.

8. Process for making a composition according to claim 1 comprising:

(a) melting components A, B and C in alkanol at about 70° C.;

(b) adding water to resultant melt at about 70° C.;

(c) separately heating to about 70° C. a surface active agent separate from any surfactant defined by component B and selected from the group consisting of avionic, nonionic, cationic, zwitterionic, amphoteric active agents, and mixtures thereof;

(d) adding said heated surfactant to solution of (a) and (b);

(e) cooling mixture of (d) to room temperature, and (f) adding cationic polymer to resultant mixture.

9. Process according to claim 8, wherein alkanol is selected from the group consisting of ethanol and glycerol.

10. A method of treating dry, aged or damaged skin which comprises applying to the skin an effective amount of the composition of claim 1.

* * * * *